(12) United States Patent
Inarejos García et al.

(10) Patent No.: US 10,933,110 B2
(45) Date of Patent: Mar. 2, 2021

(54) SAFFRON EXTRACT AND ITS USE FOR THE PREVENTION OF MOOD DISORDERS RELATED TO DEPRESSION

(71) Applicant: PHARMACTIVE BIOTECH PRODUCTS, S.L., Madrid (ES)

(72) Inventors: Antonio Manuel Inarejos García, Madrid (ES); Marin Prodanov Prodanov, Madrid (ES); Amanda Rao, Madrid (ES); Jean-Marie Raymond, Madrid (ES)

(73) Assignee: Pharmactive Biotech Products, S.L., Madrid (ES)

( * ) Notice: Subject to any disclaimer, the term of this patent is extended or adjusted under 35 U.S.C. 154(b) by 106 days.

(21) Appl. No.: 16/087,585

(22) PCT Filed: Apr. 17, 2017

(86) PCT No.: PCT/ES2017/070237
§ 371 (c)(1),
(2) Date: Sep. 21, 2018

(87) PCT Pub. No.: WO2017/182688
PCT Pub. Date: Oct. 26, 2017

(65) Prior Publication Data
US 2019/0099464 A1   Apr. 4, 2019

(30) Foreign Application Priority Data
Apr. 18, 2016   (ES) .............................. ES201630491

(51) Int. Cl.
*A61K 36/88* (2006.01)
*A61K 31/05* (2006.01)
*A61K 31/11* (2006.01)
*A61K 31/7024* (2006.01)
*A61K 31/7034* (2006.01)
(Continued)

(52) U.S. Cl.
CPC ............ *A61K 36/88* (2013.01); *A23L 29/206* (2016.08); *A23L 33/105* (2016.08); *A61K 9/0053* (2013.01); *A61K 9/2054* (2013.01); *A61K 31/05* (2013.01); *A61K 31/11* (2013.01); *A61K 31/7024* (2013.01); *A61K 31/7034* (2013.01); *A61P 25/24* (2018.01);
(Continued)

(58) Field of Classification Search
CPC ...................................................... A61K 36/88
See application file for complete search history.

(56) References Cited

FOREIGN PATENT DOCUMENTS

| WO | WO 2010/094745 A1 | 8/2010 |
| WO | WO 2015/124318 A1 | 8/2015 |

OTHER PUBLICATIONS

Chryssanthi et al., "A new validated SPE-HPLC method for monitoring crocetin in human plasma—Application after saffron tea consumption", Journal of Pharmaceutical and Biomedical Analysis, vol. 55, Feb. 21, 2011, pp. 563-568.
(Continued)

*Primary Examiner* — Rosanne Kosson
(74) *Attorney, Agent, or Firm* — Womble Bond Dickinson (US) LLP (57) ABSTRACT

The present invention relates to a powdered composition obtained from saffron stigmas characterized in that it comprises from 0.03% to 1% dry weight of safranal; and at least 3.48% dry weight of crocins that encompasses the various trans-crocin-4 (major isomer), trans-crocin-3, trans-crocin-2', cis-crocin-4, trans-crocin-2, trans-crocin-1 isomers and any of their mixtures.

4 Claims, 4 Drawing Sheets

(51) Int. Cl.
  A23L 33/105    (2016.01)
  A23L 29/206    (2016.01)
  A61K 9/20      (2006.01)
  A61P 25/24     (2006.01)
  A61K 9/00      (2006.01)
(52) U.S. Cl.
  CPC ..... *A23V 2002/00* (2013.01); *A23V 2200/322* (2013.01); *A23V 2250/211* (2013.01); *A23V 2250/2132* (2013.01)

(56) References Cited

OTHER PUBLICATIONS

Almodovar et al., "Bioaccessibility and Pharmacokinetics of a Commercial Saffron (*Crocus sativus* L.) Extract", Hindawi Evidence-Based Complementary and Alternative Medicine, vol. 2020, Jan. 31, 2020, Article ID 1575730.

Alonso et al., "Composition of Crocins and Picrocrocin from Spanish Saffron (*Crocus satnus* L.)", Journal of Food Quality, vol. 24, Jun. 1, 2000, pp. 219-233.

Mohammadpour et al., "Development and Validation of HPLC Method for Determination of Crocetin, a constituent of Saffron, in Human Serum Samples", Iranian Journal of Basic Medical Science, vol. 16, No. 1, Jan. 2013, pp. 47-55.

Rodríguez-Neira et al., "Influence of Culinary Processing Time on Saffron's Bioactive Compounds (*Crocus sativus* L.)", Plant Foods for Human Nutrition, Nov. 6, 2014, vol. 69, No. 4, pp. 291-296.

Carmona et al., "Influence of Different Drying and Aging Conditions on Saffron Constituents", Journal of Agricultural and Food Chemistry, Apr. 16, 2005, vol. 53, No. 10, pp. 3974-3979.

Atyane et al., "Influence of Different Extraction Methods and the Storage Time on Secondary Metabolites of Saffron", International Journal of Engineering Research & Technology (IJERT), vol. 6 Issue 01, Jan. 2017, pp. 65-69.

Sánchez et al., "Kinetics of Individual Crocetin Ester Degradation in Aqueous Extracts of Saffron (*Crocus sativus* L.) upon Thermal Treatment in the Dark", Journal of Agricultural and Food Chemistry, Feb. 1, 2008, vol. 56, pp. 1627-1637.

Tong et al., "Simultaneous quantification of crocetin esters and picrocrocin changes in Chinese saffron by high-performance liquid chromatography-diode array detector during 15 years of storage", Pharmacognosy Magazine, Oct. 7, 2015, vol. 11, Issue 43, pp. 540-545.

Tsimidou et al., "Stability of Saffron Pigments in Aqueous Extracts", Journal of Food Science, Sep. 1993, vol. 58, No. 5, pp. 1993-1073.

Alonso et al., "Composition of Crocins and Picrocrocin From Spanish Saffron (*Crocus sativus* L.)" Journal of Food Quality, vol. 24, Issue 3, Jun. 1, 2000, pp. 219-233.

Akhondzadeh et al., "Comparison of *Crocus sativus* L. and imipramine in the treatment of mild to moderate depression: A pilot double-blind randomized trial [ISRCTN45683816]", BMC Complementary and Alternative Medicine, vol. 4, No. 12, Sep. 2, 2004.

Akhondzadeh et al., "*Crocus sativus* L. in the Treatment of Mild to Moderate Depression: A Double-blind, Randomized and Placebo-controlled Trial", Phytotherapy Research vol. 19, No. 2, Feb. 2005, pp. 148-151.

Basti et al., "Petal and Stigma of *Crocus sativus* L. in the Treatment of Depression: A Pilot Double-blind Randomized Trial", Journal of Medicinal Plants, vol. 7, Supplement No. 4, Feb. 17, 2008, pp. 29-36.

Basti et al., "Comparison of petal of *Crocus sativus* L. and fluoxetine in the treatment of depressed outpatients: A pilot double-blind randomized trial", Progress in Neuro-Psychopharmacology & Biological Psychiatry, vol. 31, Dec. 15, 2006, pp. 439-442.

Beck et al., "Psychometric Properties of the Beck Depression Inventory: Twenty Five Years of Evaluation", Clinical Psychology Review, vol. 8, Issue. 1, 1988 pp. 77-100.

Bisschop et al. "Chronic diseases and depression: the modifying role of psychosocial resources", Social Science & Medicine, vol. 59, No. 4, Aug. 2004, pp. 721-733.

Caballero-Ortega et al., "HPLC quantification of major active components from 11 different saffron (*Crocus sativus* L.) sources", Food Chemistry vol. 100, Issue 3., Nov. 11, 2005, pp. 1126-1131.

Carr et al. "Antidepressant and anxiolytic effects of selective 5-HT6 receptor agonists in rats", Psychopharmacology (Berl), vol. 213(2-3), Feb. 2011, pp. 499-507.

Gerhard Stemmler, "Methodological Considerations in the Psychophysiological Study of Emotion", R. J.Davidson, H. H. Goldsmith, K. R. Scherer (Eds.): Handbook of Affective Science, New York: Oxford University Press, 2002, pp. 225-255.

Edwards et al., "Mood Swings: Variability in the Use of the Profile of Mood States", Journal of Pain Symptom Management, vol. 28, No. 6, Dec. 6, 2004, pp. 534.

Ettehadi et al., "Aqueous Extract of Saffron (*Crocus sativus*) Increases Brain Dopamine and Glutamate Concentrations in Rats", Journal of Behavioral and Brain Science, vol. 3, Jul. 2013, pp. 315-319.

Fava et al., "Diagnosis and Definition of Treatment-Resistant Depression", Biological Psychiatry, Apr. 15, 2003, vol. 53, No. 8, pp. 649-659.

Orfanou et al., "Evaluation of the coloring strength of saffron spice by UV-Vis Spectrometry", Food Chemistry, vol. 57, No. 3, Dec. 29, 1995, pp. 463-469.

Lopresti et al., "Saffron (*Crocus sativus*) for depression: a systematic review of clinical studies and examination of underlying antidepressant mechanisms of action", Human Psychopharmacology, vol. 29, No. 6, Sep. 22, 2014, pp. 517-527.

Maes et al., "New drug targets in depression: inflammatory, cell-mediated immune, oxidative and nitrosative stress, mitochondrial, antioxidant, and neuroprogressive pathways. And new drug candidates—Nrf2 activators and GSK-3 inhibitors", Inflammopharmacology vol. 20, No. 3, Jan. 24, 2012, pp. 12-150.

Karimi et al., "Study of antidepressant effect of aqueous and ethanolic extract of *Crocus sativus* in mice." , Iranian Journal of Basic Medical Sciences, vol. 4, No. 3, 2001.

"ISO 3632-2 : 2010(R2017): Spices—Saffron (*Crocus sativus* L.)—Part 2: Test Methods", International Organization for Standardization, May 2011.

Tarantilis et al., "Determination of saffron (*Crocus sativus* L.) components in crude plant extract using high-performance liquid chromatography-UV-visible photodiode-array detection—mass spectrometry", Journal of Chromatography A, vol. 699, Issues 1-2, Jan. 10, 1995, pp. 107-118.

Ulbricht et al., "An Evidence-Based Systematic Review of Saffron (*Crocus sativus*) by the Natural Standard Research Collaboration", Journal of Dietary Supplements, vol. 8, No. 1, 2011 2011, pp. 58-114.

Noorbala et al., "Hydro-alcoholic extract of *Crocus sativus* L. versus fluoxetine in the treatment of mild to moderate depression: a double-blind, randomized pilot trial", Journal of Ethnopharmacology, vol. 97, Jan. 6, 2005, pp. 281-284.

Ferguson et al. "SSRI Antidepressant Medications: Adverse Effects and Tolerability", Primary Care Companion Journal of Clinical Psychiatry, vol. 3 No. 1, Feb. 2001, pp. 22-27.

Kashani et al., "Saffron for treatment of fluoxetine-induced sexual dysfunction in women: randomized double-blind placebo-controlled study", Human Psychopharmacology Clinical and Experimental, vol. 28, Dec. 20, 2012, pp. 54-60.

Moshiri et al., "*Crocus sativus* L. (petal) in the treatment of mild-to-moderate depression:A double-blind, randomized and placebo-controlled trial", Phytomedicine, vol. 13, Aug. 24, 2006, pp. 607-611.

Seretti et al., "Meta-analysis of serotonin transporter gene promoter polymorphism (5-HTTLPR) association with selective serotonin reuptake inhibitor efficacy in depressed patients", Molecular Psychiatry, vol. 12, Dec. 5, 2006, pp. 247-257.

Vanderkooy et al., "Antidepressant Side Effects in Depression Patients Treated in a Naturalistic Setting: A Study of Bupropion, Moclobemide, Paroxetine, Sertraline, and Venlafaxine", Canadian Journal of Psychiatry, vol. 47, No. 2, Mar. 2002, pp. 174-180.

(56) References Cited

OTHER PUBLICATIONS

Ordoudi et al., "Saffron Quality: Effect of Agricultural Practices, Processing and Storage", Production Practices and Quality Assessment of Food Crops, vol. 1, Preharvest Practice, Springer, Dordrecht, Eds: Ramdane Dris, Shri Mohan Jain, 2004, pp. 209-260.

Hosseinzadeh et al., "Antidepressant Effect of *Crocus sativus* L. Stigma Extracts and their Constituents, Crocin and Safranal, in Mice", ISHS Acta Horticulturae 650: Ist International Symposium on Saffron Biology and Biotechnology, 2004, pp. 435-445.

Singleton et al., "Colorimetry of Total Phenolics With Phosphomolybdic-Phosphotungstic Acid Reagents", American Journal of Enology and Viticulture, vol. 16, Jan. 1, 1965, pp. 144-158.

Lovibond et al., "The Structure of Negative Emotional States: Comparison of the Depression Anxiety Stress Scales (DASS) With the Beck Depression and Anxiety Inventories", Behavioral Research and Therapy, vol. 33, No. 3, Mar. 1995, pp. 335-343.

Terry et al., "Construct validity of the Profile of Mood States—Adolescents for use with adults", Psychology of Sport and Exercise, vol. 4, Nov. 1, 2001, pp. 125-139.

Haddad et al., "Do antidepressants cause dependence?", Epidemiologia E Psichiatria Sociale, vol. 14, No. 2, Oct. 11, 2011, pp. 58-62.

Lech et al., "Saffron yellow: characterization of carotenoids by high performance liquid chromatography with electrospray mass spectrometric detection", Journal of Mass Spectrometry, vol. 44, Oct. 9, 2009, pp. 1661-1667.

Max Hamilton, "A Rating Scale for Depression", Journal of Neurology, Neurosurgery, and Psychiatry, vol. 23, Feb. 1960, pp. 56-62.

Shahmansouri et al., "A randomized, double-blind, clinical trial comparing the efficacy and safety of *Crocus sativus* L. with fluoxetine for improving mild to moderate depression in post percutaneous coronary intervention patients", Journal of Affective Disorders, vol. 155, Feb. 2014, pp. 216-222.

Moussavi et al., "Depression, chronic diseases, and decrements in health:results from the World Health Surveys", Lancet, vol. 370, Sep. 8, 2007, pp. 851-858.

Leonard et al., "Mechanistic explanations how cell-mediated immune activation, inflammation and oxidative and nitrosative stress pathways and their sequels and concomitants play a role in the pathophysiology of unipolar depression", Neuroscience and Behavioral Reviews, vol. 36, Dec. 10, 2011, pp. 764-785.

Maes et al., "A review on the oxidative and nitrosative stress (O&NS) pathways in major depression and their possible contribution to the (neuro)degenerative processes in that illness", Progress in Neuro-Psychopharmacology & Biological Psychiatry, vol. 35, May 12, 2010, pp. 676-692.

Fava et al., "Definition and Epidemiology of Treatment-Resistant Depression", The Psychiatric Clinics of North America, vol. 19, No. 2, Jun. 1996, pp. 179-200.

Buysse et al., "The Pittsburgh Sleep Quality Index: A New Instrument for Psychiatric Practice and Research", Psychiatry Research, vol. 28, Nov. 12, 1998, pp. 193-213.

Palta et al., "Depression and Oxidative Stress: Results From a Meta-Analysis of Observational Studies", Psychosomatic Medicine, Dec. 12, 2013, vol. 76, No. 1.

Watson et al., "The PANAS-X: Manual for the Positive and Negative Affect Schedule—Expanded Form", Iowa Research Online, Department of Psychological and Brain Sciences Publications, Aug. 1, 1999, downloaded from: https://ir.uiowa.edu/psychology_pubs/11/.

Lage et al., "Quantification of Saffron (*Crocus sativus* L.) metabolites crocins, picrocrocin, and safranal for quality determination of the spice grown under different environmental Moroccan conditions", Scientia Horticulturae, vol. 121, Issue 3, Jul. 2, 2009, pp. 366-373.

International Search Report and Written Opinion of the International Searching Authority dated Sep. 15, 2017 for PCT Application No. PCT/ES2017/070237.

Bergonzi, et al., "Identification and quantification of constituents of Gardenia jasminoides Ellis (Zhizi) by HPLC-DAD-ESI-MS", Food Chemistry, Mar. 6, 2012, vol. 134, pp. 1199-1204.

Fournier, et al., "Antidepressant Drug effects and Depression Severity: A Patient-Level Meta-Analysis", JAMA, vol. 303, No. 1, Jan. 6, 2010.

Finniss, et al., "Biological, clinical, and ethical advances of placebo effects", Lancet, vol. 375, Feb. 20, 2010, pp. 686-695.

Cai, et al., "Optimization of ultrasound-assisted extraction of gardenia fruit oil with bioactive components and their identification and quantification by HPLC-DAD/ESI-MS2", Royal Society of Chemistry, Food & Function, Jul. 2015, vol. 6, No. 7, pp. 2194-2204.

Feng, et al., "Preparative separation of crocins and geniposide simultaneously from gardenia fruits using macroporous resin and reversed-phase chromatography", Journal of Separation Science, vol. 37, No. 3, Dec. 17, 2013, pp. 314-322.

Zeka, et al., "Petals of *Crocus sativus* L. as a potential source of the antioxidants crocin and kaempferol", Fitoterapia, vol. 107, May 20, 2015, pp. 128-134.

Serefko, et al., "Magnesium in depression", Pharmacological Reports, vol. 65, Jan. 8, 2013, pp. 547-554.

Gabriel, et al., "Antidepressant discontinuation syndrome", Canadian Medical Association Journal, vol. 189, No. 21, May 29, 2017, E747.

"ISRCTN Registry ISRCTN45683816: Comparison of *Crocus sativus* L. and imipramine in the treatment of mild to moderate depression: a pilot double-blind randomised trial", last edited date: Sep. 8, 2007, available online at: <http://www.isrctn.com/ISRCTN45683816>.

SAFFRON EXTRACT AND ITS USE FOR THE PREVENTION OF MOOD DISORDERS RELATED TO DEPRESSION

CROSS-REFERENCE TO RELATED APPLICATIONS

The present patent application is a national phase application of International Application No. PCT/ES2017/070237, filed Apr. 17, 2017, which claims priority to Spanish Patent Application No. P201630491, filed Apr. 18, 2016, the disclosures of which are incorporated herein by reference.

The present invention relates to the manufacture, use and composition that comprises an extract of saffron stigmas (*Crocus sativus* L.) obtained on an industrial scale for use as a medicament. Specifically, it relates to a composition that is effective in preventing mood disorders related to depression.

This invention falls within the field of the pharmaceutical industry, specifically, within the field of prevention of mood disorders related to depression.

The saffron extract of the present invention is standardized to safranal and crocins by means High Performance Liquid Chromatography (HPLC), which are active substances related to the inhibition of the reuptake of mood-related neurotransmitters. This exact is presented as a natural alternative to avoid the use of synthetic antidepressants, which have multiple associated contraindications and disadvantages. The present invention determines the effective dose and appropriate concentration of safranal and crocins in the final extract analyzed by means of HPLC as a critical condition for the efficacy of the product in the prevention of mood disorders related to depression, as demonstrated by a clinical study in which 128 individuals participated.

SECTOR OF THE INVENTION

The application of the present invention falls within the field of the pharmaceutical industry, specifically, within the field of prevention of mood disorders related to depression.

STATE OF THE ART

After hypertension, depressive disorders are the most common medical conditions in developed countries (Akhondzadeh et al., 2008). The world Health Organization (WHO) defines them as the most common medical disorders, affecting a high percentage of the population. The most common symptoms are weight loss, anxiety, hypochondriasis, insomnia, somatic and sexual disorders, feelings of guilt, suicidal thoughts, etc. (Hamilton, 1960) Long periods of depression can lead to the onset of chronic pathologies such as heart disease and metabolic diseases such as diabetes or hormone disorders, among others (Moussavi et al., 2007; Bisschop et al., 2004).

Since one of the main causes of the onset of depression is the decline in certain mood-related neurotransmitters (Carr et al., 2011; Lopresti and Drummond, 2014), currently the most widely used antidepressants are selective inhibitors of the reuptake of these neurotransmitters (Serretti et al., 2007). Among the main neurotransmitters responsible for mood, serotonin, norepinephrin (noradrenalin) and dopamine stand out. A very well-known example is fluoxetine (Noorbala et al., 2005), which inhibits the reuptake of neurotransmitters through transporters present in presynaptic neurons, leading to increased concentrations of neurotransmitters in extracellular space.

One of the main disadvantages of synthetic drug treatments is the occurrence of side effects, which can go from mild symptoms, like dry mouth, headaches, nausea, diarrhea, etc., to severe ones, like tachycardias, sexual dysfunction, hypertension, hypercholesterolemia, etc. (Ferguson, 2001; Vanderkooy, 2002). In addition, these treatments may interact with other medicaments, they cannot be interrupted immediately and, in many cases, they may cause addiction (Haddad, 2005).

It is also worth noting that between 29 and 46% of patients who undergo treatments based on antidepressant drugs with adequate dose and duration do not show a positive response to the treatment (Fava et al., 1996, 2003).

Due to the stringent safety requirements of antidepressant treatments and the associated side effects, in recent years, research has focused on plant extracts with possible psychopharmacological application. Among them are found the saffron-based products (*Crocus sativus* L.), the effects of which have been scientifically demonstrated in both in vivo studies on experimental animals as well as in clinical studies on people who presented pathologies related to depression (Akhondzadeh, 2004, 2005, 2008; Basti et al., 2007; Noorbala et al., 2005; Moshiri et al., 2006; Ulbricht et al., 2011; Kashani, 2013; Shahmansouri et al., 2014). These scientific investigations have shown that safranal and crocins found in studied saffron extracts are responsible for the increase in concentration of neurotransmitters in brain tissue (Karimi et al., 2001; Hosseinzadeh et al., 2004; Noorbala et al., 2005; Ettehadi et al., 2013). Crocins act as dopamine and norepinephrine reuptake inhibitors whereas safranal acts as reuptake inhibitor of serotonin (Hosseinzadeh et al., 2004), thereby making treatment with saffron extracts effective provided both crocins and safranal are present in appropriate concentrations. Safranal (2,2,6-trimethyl-1,3-cyclohexadiene-1-carboxaldehyde) is the main component responsible for the aroma of saffron and which accounts for more than 60% of the total aromatic compounds (Ordundi and Tsimidou, 2004). Crocins are glycosylated esters of the dycarboxylic carotenoid crocetin, and are formed by several glycosidic esters, mainly trans- and cis-crocins 3 and 4 (Alonso et al., 2001). They differ from other vegetable-origin carotenoids because of their solubility in water and they have an intense red-orange color characteristic of saffron.

Mood disorders related to depression are often associated with high oxidative stress and, consequently, a deficit in exogenous antioxidants (Maes et al., 2011; Maes et al., 2012; Palta et al., 2014). During depression, the concentrations of enzymes that act as endogenous antioxidants decrease, these are mainly superoxide dismutase, catalase, and glutathione peroxidase, while concentrations of malonaldehyde increase, which acts as a marker of oxidative stress (Lopresti et al., 2014) together with certain products derived from the oxidation of polyunsaturated fatty acids (such as 4-hydroxyalkenals). All this promotes immune, inflammatory and, in some cases, neurodegenerative responses (Leonard and Maes, 2012). In all cases, the presence of exogenous antioxidants helps to prevent the onset of oxidative stress (Maes et al., 2011; Maes et al., 2012; Palta et al., 2014), as in the case of natural extracts derived from saffron.

In order to determine the quality of saffron, the International Standardization Organization (ISO) proposed a method of analysis called ISO3632 (1980, 1993), which enables plant quality to be quickly and easily categorized by means of spectrophotometric measurement.

It is the method of analysis of the compounds responsible for the quality of saffron by means of ISO3632 standard, which guarantees the content of these active substances in sold products. It is a quick and easy spectrophotometric method that measures absorbance at 257 nm ($\lambda_{max}$ of Picrocrocin), at 330 nm ($\lambda_{max}$ of Safranal) and at 440 nm ($\lambda_{max}$ of Crocins) of a solution of saffron extract. This method is used to categorize the quality of saffron stigmas but has finally been accepted for the analysis of bioactive compounds of saffron extracts.

There are several saffron-based products on the market, however, they often comprise a much lower proportion of the safranal and crocin active compounds than indicated, since the composition of these products is only assessed by ISO3632 standard, a spectrophotometric method that is not sufficiently selective, objective or accurate for determining these active substances, as pointed out by several studies after the publication of the ISO standard (Tarantilis et al., 1995; Orfanou and Tsimidou, 1996). Alonso et al. (2001) found that at 257 and 330 nm wavelengths, which respectively determine picrocrocin and safranal according to ISO3632 standard, there were interferences of other compounds, mainly crocin isomers, which are predominant in saffron and which produce an overestimated value of the safranal content.

The use of the ISO3632 method can adjust the content of active substances in saffron extracts according to their absorbance, enabling a saffron extract that has no safranal in its composition to also emit a 330 nm signal. This effect is mainly due to certain crocin isomers, as mentioned above, which produces a masking of the actual quality of the product. This kind of formulation is clearly detrimental to the quality of these products and this can significantly contribute to the loss of consumer confidence.

Therefore, in light of the foregoing, there exists in the state of the art a need to provide a composition based on a natural saffron extract containing the appropriate concentrations of crocins and safranal, objectively analyzed in the saffron extract, in order to effectively prevent mood disorders related to depression, without the negative side effects associated with the use of drugs.

BRIEF DESCRIPTION OF THE INVENTION

The present invention relates to a composition comprising an extract of saffron stigmas for its use as an effective medicament in the prevention of mood disorders related to depression. The extract is presented as a natural alternative with the aim of improving mood, preventing mood disorders related to depression and avoiding the need for treatment with synthetic antidepressants that have multiple contraindications and side effects.

This invention describes a process for obtaining, standardizing and using a new saffron extract, having its main bioactive compounds safranal and crocins analyzed by HPLC, related to the prevention of depressive disorders, which are also primarily responsible for the organoleptic characteristics of saffron (aroma and color, respectively). The extract object of the present invention is a natural alternative to prevent disorders related to depression, with the aim of avoiding treatment with synthetic antidepressants.

As indicated above, the compositions based on saffron extracts currently on the market have been certificated by applying the method stipulated in ISO3632 standard, which results are in much lower proportions of the safranal and crocin active compounds than indicated because it is a spectrophotometric method that is not sufficiently selective, objective or accurate for determining these active substances (see example 2). As a consequence, saffron extracts currently existing on the market do not have the appropriate amount of active substances to exert their preventive effect on disorders related to depression. In order to avoid this problem, the inventors have introduced a prior step for separating said active substances for their individualized qualification by means of Reverse Phase High Performance Liquid Chromatography (RP-HPLC), and thus determine the objective concentrations of the therapeutically active molecules, i.e., safranal, crocins and picrocrocins (see Example 1). Thanks to this novel method for the analysis of saffron, the present invention relates to a process for obtaining saffron extract and to the therapeutic use thereof, which differs from other extracts currently on the market in that it is objectively certificated for those active substances (safranal/crocins) that have the preventive effect against mood disorders related to depression. This composition guarantees an adequate balance between safranal/crocins in the final extract, which has furthermore shown to be effective in a double-blind clinical trial carried out with 128 participants who were given a dose of 28 mg/day of extract during one month, registering a significant improvement in overall mood (see Example 3).

Therefore, the present invention has the following advantages:

The safranal and the crocins of the extract of the present invention, analyzed by HPLC, are found in greater proportion than in other marketed saffron extracts characterized by ISO3632 standard.

The extract of the present invention has been found to have a functional effect on the improvement of mood in healthy individuals, specifically, it has been shown to reduce patients' tension, depression, anger, fatigue, anxiety, stress and confusion, while also increasing their vigor.

The extract of the present invention can be used as a food supplement.

The extract of the present invention does not have side effects associated with marketed synthetic antidepressants and anxiolytics.

In view of the foregoing, a first aspect of the present invention relates to a powdered composition comprising an extract of saffron stigmas analyzed by HPLC and characterized in that it comprises:

a) between 0.03% and 1% dry weight in safranal, and b) at least 3.48% dry weight of crocins, wherein said crocins comprise trans-crocin-4 (major isomer), trans-crocin-3, trans-crocin-2', cis-crocin-4, trans-crocin-2, trans-crocin-1 and/or any of their mixtures.

A second aspect of the present invention relates to the use of the composition, as described above, for the formulation of a medicament.

A third aspect of the present invention relates to the use of the composition, as described above, for preparing a medicament for the prevention of mood disorders. Mood disorders is understood as disorders associated with depression, such as fatigue, stress and anxiety, among others.

A fourth aspect of the present invention relates to the use of the composition, as described above, as a food supplement.

A fifth aspect of the present invention relates to a functional food comprising the composition, as described above.

DETAILED DESCRIPTION OF THE INVENTION

In order to obtain the saffron extract of the invention, first there is a strict selection of raw material, based mainly on determining the active substances of safranal and crocins by HPLC, microbial load, etc.

Industrial extraction of the active substances of the selected saffron stigmas is preferably carried out with water or hydroalcoholic mixtures, as long as the proportion of ethanol does not exceed 20% (v/v). Temperature control during the extraction process is critical and it must be limited to 70° C. in order to avoid the deterioration of certain crocin isomers that could be affected under higher temperatures. Organic solvents such as ethyl acetate, hexane, petroleum ether, acetone, methanol, or the like, are not allowed for obtaining the saffron extract object of the present invention.

The raw extract takes on the form of a dense red-colored liquid with the intense aroma characteristic of saffron, which it is cooled at room temperature with subsequent removal of moisture, and different drying techniques can be used for this stage, provided the temperature does not exceed 70° C.

The last step consists of adjusting the size of the particle by grinding the dry extract in a hammer mill or a knife mill, controlling the grinding temperature at all times so that it does not affect the bioactive compounds, and sieving the grind through a sieve with a maximum mesh of 240 µm. The raw extract is mixed with a pharmaceutically acceptable excipient until the formula of the present invention is obtained. Non-limiting examples of excipients are starch, lactose, dextrose, maltodextrin, sucrose, mannitol, sorbitol, glucose, microcrystalline cellulose, di- and tricalcium phosphate, calcium sulfate, Kaolin and sodium chloride. Preferably, the excipient is obtained from dextrin, maltodextrin or any of their mixtures.

Therefore, a first aspect of the present invention relates to a powdered composition comprising an extract of saffron stigmas analyzed by HPLC and characterized in that it comprises:
a) Between 0.03% and 1% dry weight of safranal, and
b) At least 3.48% dry weight of crocins, wherein said crocins comprise trans-crocin-4 (main isomer), trans-crocin-3, trans-crocin-2', cis-crocin-4, trans-crocin-2, trans-crocin-1 and/or any of their mixtures.

Preferably, the composition, as described above, comprises:
a) Between 0.03% and 0.50% dry weight of safranal,
b) Between 3.48% and 8.00% dry weight of crocins.
More preferably, the composition, as described above, comprises:
a) Between 0.03% and 0.50% dry weight of safranal,
b) Between 3.48% and 7.00% dry weight of crocins.
Even more preferably, the composition, as described above, comprises:
a) Between 0.03% and 0.35% dry weight of safranal,
b) Between 3.48% and 6.00% dry weight of crocins.

In another more preferred embodiment of the composition, as described above, the composition is characterized in that it comprises, with respect to the amount of total crocins of the composition, between 45% and 65% dry weight of trans-crocin-4, between 15% and 30% dry weight of trans-crocin-3, between 0.3% and 5% dry weight of trans-crocin-2', between 0.3% and 10% dry weight of cis-crocin-4, between 0.3% and 15% dry weight of trans-crocin-2, between 0.5% and 5% dry weight of trans-crocin-1 and/or any of their mixtures.

In another more preferred embodiment of the composition, as described above, the composition is characterized in that it comprises, with respect to the amount of total crocins of the composition, 53% dry weight of trans-crocin-4, 22% dry weight of trans-crocin-3, 1% dry weight of trans-crocin-2', 2% dry weight of cis-crocin-4, 3% dry weight of trans-crocin-2, 2% dry weight of trans-crocin-1 and/or any of their mixtures.

In another embodiment of the first aspect of the present invention, the composition, as described above, further comprises picrocrocin, the content of which in the extract of the present invention, analyzed by HPLC according to the method proposed by Caballero-Ortega et al., (2007), comprises at least 2.5% expressed in g of p-nitroaniline per 100 g of dry extract.

In another embodiment of the first aspect of the present invention, the composition, as described above, further comprises a concentration of total polyphenols analyzed by means of the Folin-Ciocalteu reagent (Singleton and Rossi, 1965), of at least 1.0% expressed as gallic acid per 100 g of dry extract.

In another embodiment of the first aspect of the present invention, the composition as described above comprises:
a) Between 0.03% and 0.35% dry weight of safranal,
b) Between 3.48% and 6.00% dry weight of crocins,
c) At least 2.5% expressed in g of p-nitroaniline per 100 g of dry extract, and
d) At least 1.0% gallic acid per 100 g of dry extract.

In another embodiment of the first aspect of the present invention, the composition, as described above, has a particle size of less than 240 µm.

In another embodiment of the first aspect of the present invention, the composition, as described above, also comprises at least one pharmaceutically accepted excipient.

The term "excipient" refers to a substance which helps to absorb any of the components of the product of the invention, stabilizes said components or helps in the preparation of the pharmaceutical composition. Thus, excipients can have the function of keeping the components bound together, such as for example starches, sugars or celluloses, a sweetening function, a colorant function, the function of protecting the medicament from the external medium, such as for example isolating it from the air and/or moisture, a filler function for a tablet, capsule or any other form of formulation, such as for example dibasic calcium phosphate, a disintegrating function to facilitate the dissolution of the components and their absorption in the intestine, without excluding other types of excipients not mentioned in this paragraph. Therefore, the term "excipient" is defined as the substance which, included in dosage forms, is added to the active substances or their associations in order to enable their preparation and stability, modify their organoleptic properties or determine the physical/chemical properties of the pharmaceutical composition and its bioavailability. The "pharmaceutically acceptable" excipient should not interact with the activity of the active compounds of the pharmaceutical composition. Examples of excipients are binding agents, fillers, disintegrants, lubricants, coatings, sweeteners, flavorings and colorants. More specific, non-limiting examples of acceptable excipients are starches, sugars, xylitol, sorbitol, calcium phosphate, steroid fats, talc, silica or glycerin, among others.

In a preferred embodiment of the first aspect of the present invention, the composition is a pharmaceutical composition and comprises pharmaceutically acceptable excipients. The pharmaceutical composition is the formulation of the set of components making up at least the product of the invention (the composition comprising a saffron extract), which has at least one application in improving the physical, physiological and/or psychological condition of a subject, implying an overall improvement of their health as well as an increase in their quality of life.

In the present invention the term "subject" is equivalent to the term "individual", whereby both terms can be used interchangeably in the present invention. "Subject" means any animal belonging to any species. Examples of subjects include, but are not limited to, commercially bred animals such as birds (hens, ostriches, chickens, geese, partridges, etc.), rabbits, hares, domestic animals (dogs, cats, etc.), livestock such as sheep and goat livestock, pigs, wild boars, horses, ponies, etc., and cattle (bulls, oxen, etc.). In a particular embodiment, the subject is a mammal, preferably a primate, more preferably a human being of any race, sex or age.

A second aspect of the present invention relates to the use of the composition, as described above, for the preparation of a medicament. The medicament comprises the composition in a therapeutically effective dosage. As used herein, the term "therapeutically effective dosage" relates to the concentration of the components of interest of the pharmaceutical composition, which, when administered, is capable of producing clear preventive effects of an illness or studied pathological condition, as defined here below.

A third aspect of the present invention relates to the use of the composition, as described above, for preparing a medicament for the prevention of mood disorders related to depression.

In the present invention "prevention" means avoiding the occurrence of the illness or pathological condition in an individual, specifically, when said individual is predisposed to the pathological condition, but as yet has not been diagnosed to suffer from it. In the present invention, the illness or pathological condition is a mood disorder related to depression.

"Disorder" is understood as the behavioral or psychological pattern of clinical significance that, whatever its cause, is an individual manifestation of a psychological or biological dysfunction. This manifestation is considered a symptom when it is associated with discomfort (for example, pain), to a disability (for example, deterioration in an area of functioning), or a significantly increased risk of dying or suffering pain, disability or loss of freedom. In the present invention, "mood disorders" are understood as the set of disorders defined in the *Diagnostic and Statistical Manual of Mental Disorders*, abbreviated as DSM IV TR, the main underlying characteristic of which would be an alteration of the individual's mood. The International Classification of Diseases or ICD 10, classifies these disorders under the heading "Mood Disorders (Affective)". Two groups of mood disorders are usually differentiated depending on whether or not they include episodes of mania or hypomania: depressive disorders and bipolar disorders. In the context of the present invention, the composition, as described above, is aimed at the prevention of mood disorders related to depression. Examples of mood disorders related to depression include, but are not limited to, atypical depression, melancholic depression, depressive psychosis, catatonic depression, postpartum depression, seasonal affective disorder, dysthymia, double depression, unspecified depressive disorder, personality depressive disorder, brief recurrent depressive disorder, and minor depression.

In an embodiment of the second and third aspects, the composition, as described above, is administered orally.

In another embodiment of the second and third aspects, the composition, as described above, is administered in a dosage greater than 15 mg/day, preferably, the daily dosage is between 20 and 40 mg/day, more preferably, the daily dosage is between 25 and 31 mg/day, still more preferably, the daily dosage is between 25 and 28 mg/day, and even more preferably, the daily dosage is 28 mg/day.

For its therapeutic application, the product of the invention will be in a pharmaceutically acceptable or substantially pure form, that is, having a pharmaceutically acceptable grade of purity, excluding the usual pharmaceutical additives such as diluents and carriers and not including material considered toxic at normal dosage levels.

The grades of purity of the saffron extract of the present invention are greater than 50%, preferably greater than 70%, and still more preferably greater than 90%. The "dosage form or pharmaceutical form" is the arrangement to which the active substances and excipients adapt in order to form a medicament. It is defined by the combination of the form in which the pharmaceutical composition is presented by the manufacturer and the form in which it is administered.

The pharmaceutical composition may comprise a "vehicle" or carrier, which is preferably an inert substance. The function of the vehicle is to facilitate the incorporation of other compounds, to allow a better dosing and administration or to give consistency and shape to the pharmaceutical composition. Therefore, the vehicle is a substance that is used to dilute any of the components of the pharmaceutical composition of the present invention to a determined volume or weight, or even without diluting said components it is capable of allowing better dosing and administration or giving consistency and shape to the medicament. Due to all of this, a vehicle would be considered pharmaceutically acceptable. When the extract is presented in liquid form, the pharmaceutically acceptable vehicle is the diluent. In addition, the excipient and the vehicle must be pharmaceutically acceptable. The pharmaceutical composition of the invention may comprise other active substances. In addition to the requirement of therapeutic effectiveness, where said pharmaceutical composition may require the use of other therapeutic agents, there may be additional fundamental reasons that compel or strongly recommend the use of a combination of a compound of the invention and another therapeutic agent. The term "active substance" is any matter, regardless of its origin, human, animal, plant, chemical or other, to which a specific activity is attributed in order to constitute a medicament.

In each case, the form of presentation of the medicament will be adapted to the chosen route of administration. Thus, the composition of the present invention may be presented in the form of solutions or any other form of clinically permitted administration and in a therapeutically effective dosage. The pharmaceutical composition of the invention may be presented in solid, semi-solid, liquid or gaseous form; as a tablet, capsule, powder, granule, ointment, solution, suppository, injection, inhalant, gel syrup, nebulizer, microsphere or aerosol. Preferably, the composition is adapted for oral administration, for example in the form of a tablet, capsule, powder, granule solution or syrup.

In another embodiment of the second and third aspects, the composition, as described above, is administered as a tablet, capsule, powder, granule or solution.

The previously mentioned compositions may be prepared using conventional methods, such as those described in the Pharmacopeias of different countries and other reference texts. The compounds and compositions of the present invention may be administered together with other medicaments in combined therapies.

In addition to what is described in previous paragraphs, the present invention also contemplates the possibility that the composition, as described above, may be administered to a subject together with other compounds, whether or not these form part of the composition.

A fourth aspect of the present invention relates to the use of the composition, as described above, as a food supplement. "Food supplement" is understood as the products marketed in the form of capsules, tablets, phials, herbal infusions, drinkable solutions, etc., intended to supplement the usual diet and which constitute a concentrated source of nutrients (such as vitamins, minerals, amino acids, essential fatty acids, fiber, etc.) or other substances that have a nutritional or physiological effect.

A fifth aspect of the present invention relates to a functional food comprising the composition, as described above. A functional food is a food that, beyond satisfying nutritional needs, is able to produce a specific beneficial effect on health, associated with the prevention or reduction of the risk of contracting specific pathologies. This beneficial effect is mainly achieved by adding, modifying or eliminating certain components present in foods.

Within the context of the present invention, methods of treatment equivalent to the uses described in the present description are also contemplated. Thus, in another aspect, the invention is associated to a method for preventing mood disorders related to depression in a subject that comprises administering a composition to said subject as described above.

Throughout the description and the claims, the word "comprises" and its variants are not intended to exclude other technical characteristics, additives, components or steps. For those skilled in the art, other objects, advantages and characteristics of the invention may be deduced from both the description and the practical use of the invention. The following examples and drawings are provided by way of illustration, and are not meant to limit the present invention.

EXAMPLES

The invention is illustrated below by the trials conducted by the inventors, which demonstrate the composition and the activity of the composition of the invention.

Example 1—Determining the Concentration of the Bioactive Compounds in the Composition of the Invention Firstly, saffron stigmas were selected based on the quality thereof (saffron from crops in Castilla-La Mancha, Spain) and macerated in water at a temperature lower than 70° C. and stirred. Then, a more exhaustive concentration was performed without exceeding a temperature of 70° C., and a raw dry extract was obtained, which was subsequently diluted with dextrin until obtaining a minimum concentration in safranal and crocins of 0.03% and 3.48% on a dry basis respectively.

The quantitative analysis of the bioactive compounds of the saffron extract thus obtained is performed in a 1260 Infinity Series HPLC system coupled to a "Diode Array" detector (Agilent Technologies, Palo Alto, Calif., USA). The chromatographic separation was carried out by a C18 column (250 mm/4.6 mm/5 µm; ACE-5 PFP, Scotland) at 25° C. and a flow rate of the mobile phase of 1 mL/min. The mobile phase was made up of a component A) water: acetonitrile (85:15, v/v) and component B) methanol, with a linear gradient of 10 to 100% of methanol in 60 min. Both the samples of the extract of the present invention and the reference standards were diluted in a methanol:water solution (50:50, v/v). The elution of the picrocrocin, safranal and crocins was monitored at absorbance values of 250, 310 and 440 nm, respectively (Caballero-Ortega et al., 2007). The quantification of these compounds was carried out by external calibration curves of p-nitroaniline (Sigma Aldrich, St. Louis, Mo., USA) to quantify the picrocrocin, safranal (Sigma Aldrich, St. Louis, Mo., USA) to quantify the safranal, and the trans-crocin-4 isomer (Phytolab, Hamburg, Germany) to quantify the different crocin isomers.

Figure 1:
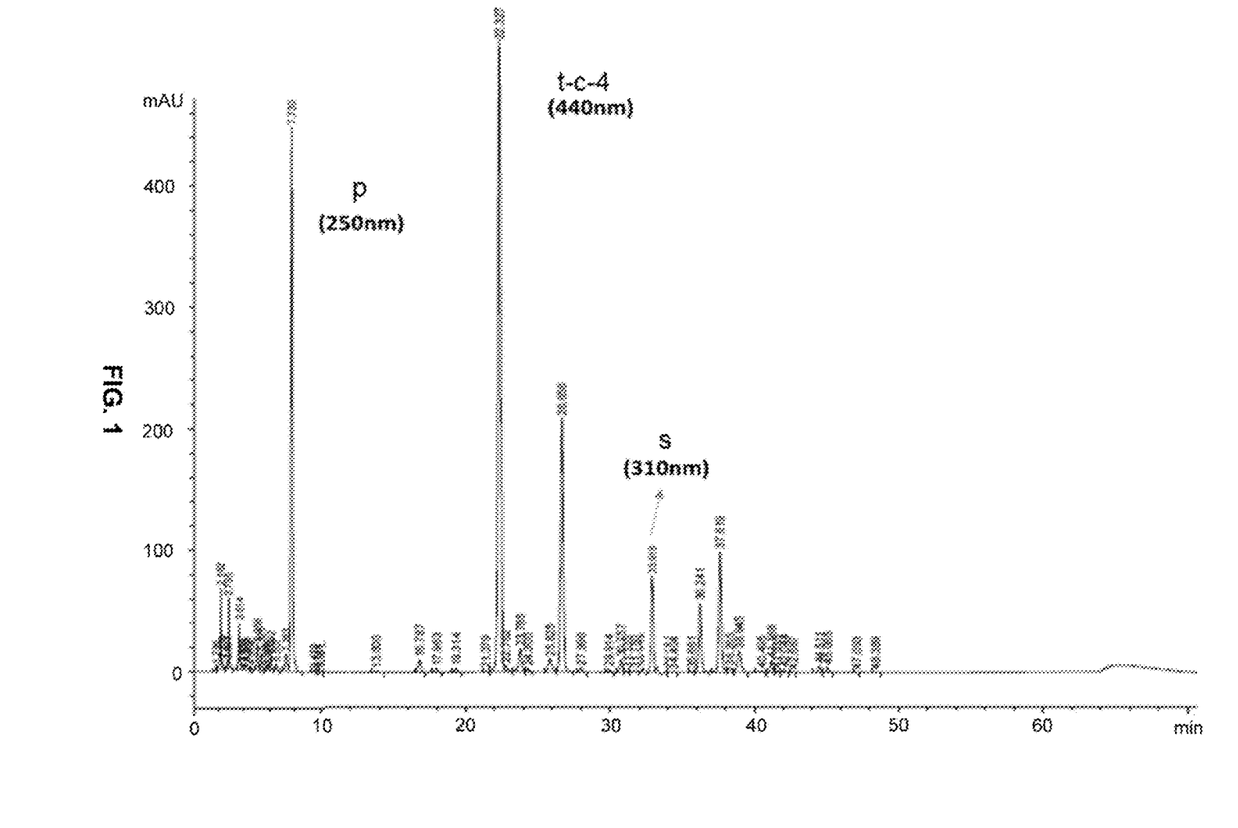
FIG. 1. Overlaid HPLC chromatograms of the main components of the saffron extract of the invention. P: Picrocrocin; t-c-4: trans-Crocin-4; s: Safranal.

FIG. 1 shows the overlaid chromatogram, acquired for wavelengths at 250, 310 and 440 nm of the saffron extract of the invention, in the aforementioned chromatographic conditions. At 250 nm, a peak may be seen with a retention time (rt) of 7.6 minutes, which corresponds to picrocrocin, whilst at 310 nm, another peak may be seen with a rt of 33.9 minutes, which corresponds to safranal. In the chromatogram recorded at 440 nm, now in the visible spectrum, there are different crocin isomers, the greatest peak corresponding to the trans-crocin-4 isomer (minute 22.3).

To confirm the identity of each peak, an analysis of the masses of each molecule found in the extract of the present invention was also carried out. In order to do so, an Agilent series 1100 system (Palo Alto, Calif., USA) was used connected to a quadrupole mass spectrometer detector (Hewlett-Packard, series 1100 MSD) with an electrospray ionization source (ESI), which worked both positively and negatively. The mass range was 50 to 1500 u, the drying gas flow was 10 L/minutes, drying gas temperature was 340° C., nebulizer pressure was 40 psig, vaporizer temperature was 150° C., capillary voltage was 2000V, and charging voltage was 2000V.

Table 1, below, shows the individual analysis of the main crocin isomers, found in the saffron extract of the present invention at 440 nm, along with the main bioactive compounds found at 250 nm (picrocrocin and kaempferol diglucoside) and 310 nm (safranal). All the UV-VIS spectra of the crocin isomers had maximums close to 250, 310 and 440 nm in common, and the main quasi-ions and fragments analyzed correspond to those found by Lech et al., (2009) in strands of saffron, where the ESI+ mode was the most effective in determining each one of these carotenoids. Picrocrocin shows a maximum at 251 nm, safranal also shows a single maximum at 313 nm, while kaempferol diglucoside has a spectrum characteristic of this flavonoid with maximums at 265 and 346 nm. The rest of the crocin isomers found in the saffron extract of the present invention showed the same spectrum characteristic of this carotenoid, as shown in Table 1, with maximums around 257, 330 and 440 nm.

Commercially available reference standards were also used to identify trans-crocin-4 and safranal, from which solutions were prepared and subjected to the same analysis conditions as those used for the extract certificated by HPLC, object of the present invention.

TABLE 1

Compounds identified in the chromatogram of FIG. 1, with ESI-MS detection in positive ion (ESI+) and negative ion (ESI−) mode.

| RT (minutes) | Compound | Maximum UV-Vis (nm) | ESI+ (m/z) | ESI− (m/z) |
|---|---|---|---|---|
| 7.6 | Picrocrocin | 251 | 511.2; 365.1; 353.2; 337.1; 329.1; 185.1; 159.9; 151.1; 123.0; 81.3 | 1480.8; 667.2; 517.1; 385.0; 181.2; 153.1 |
| 11.5 | Kaempferol diglucoside | 266; 347 | 633.2; 347.1 | 609.0; 284.0 |
| 16.7 | | 262; 325; 442; 467 | | |
| 17.8 | | 223; 270; 429; 438 | | |
| 18.0 | | 223; 270; 327; 419; 440 | | |
| 19.3 | | 261; 441; 465 | | |
| 22.1 | trans-crocin-4 | 261; 323; 441; 464 | 999.4; 675.2; 511.2; 347.1 | 1336.2; 651.2; 326.8; 283.1 |
| 22.7 | | 261; 440 | 999.2; 742.8; | |
| 23.8 | | 261; 323; 439; 462 | 717.0; 510.9; 347.0 | |
| 24.2 | | 260; 439; 461 | | |
| 26.0 | | 262; 323; 440; 463 | | |
| 26.7 | trans-crocin-3 | 261; 323; 440; 463 | 837.4 | |
| 27.9 | | 261; 438; 462 | | |
| 29.8 | | 260; 437; 462 | | |
| 30.7 | trans-crocin-2' | 261; 328; 440; 464 | 675.2; 593.0; 513.2; 351.1; 130.1; 102.2; 74.1 | |
| 31.2 | | 460 | | |
| 32.3 | | 243; 305; 420; 441 | | |
| 32.6 | | 243; 305; 420; 441 | | |
| 33.9 | Safranal | 313 | | |
| 36.2 | cis-crocin-4 | 225; 262; 325; 433; 456 | 999.4; 821.3; 668.3; 611.0; 391.0; 347.0 | 651.2 |
| 37.6 | trans-crocin-2 | 260; 322; 433; 458 | 675.2; 541.1 | 651.2; 327.1; 311.1; 283.1 |
| 38.7 | | 224; 262; 225; 432; 455 | | |
| 41.1 | trans-crocin-1 | 224; 259; 318; 433; 458 | 768.8; 748.8; 575.2; 513.2; 473.2; 351.1 | |

The sections in "bold" correspond to quasi-molecular ions (999.4; 837.4; 675.2; 633.2; 609.0; 513.2; 511.2; 353.2 m/z) or ionic fragments (151.1; 123.0 m/z), which coincide with the work carried out by Lech et al., (2009).

Due to the fact that safranal and crocins are the active substances related to mood improvement, these were quantified together as the sum of the safranal concentrations and the different crocin isomers in g/100 g of dry matter (%), according to the chromatograms obtained from the previously described HPLC analysis. Calibration curves were used, representing area units compared to concentration (mg/L), in order to quantify them, which were obtained through the analysis of the commercial reference substances safranal and the trans-crocin-4 at 310 and 440 nm respectively. The concentration of these compounds in the saffron extract of the present invention was calculated using the formula (1), taking into account the humidity of said extract and the purity of the reference substances used.

$$(\%) = \frac{(A_{310nm} - a_{310nm})/m_{310nm} + (\Sigma A_{440nm} - a_{440nm})/m_{440nm}}{C} \times 100 \quad (1)$$

Where:
In the saffron extract of the present invention:
$A_{310nm}$ is the peak area of safranal at 310 nm.
$\Sigma A_{440nm}$ is the sum of the areas of the peaks corresponding to the different crocin isomers at 440 nm.
C is the concentration of the extract (mg/L)
In the reference substances:
$a_{310nm}$ is the ordinate in the origin of the calibration curve of the safranal standard
$a_{440nm}$ is the ordinate in the origin of the calibration curve of the trans-crocin-4 standard
$m_{310nm}$ is the slope of the calibration curve of the safranal standard
$m_{440nm}$ is the slope of the calibration curve of the trans-crocin-4 pattern Among the active substances quantified in the above formula (1), crocins are the major compounds. Safranal is found in a smaller proportion, but its presence is essential in the saffron extract in order to obtain the desired effect in the prevention of mood disorders related to depression.

Example 2—HPLC Analysis of Commercial Saffron Extracts, Certificated in Safranal According to the ISO3632 Standard Five commercial saffron extracts were analyzed by HPLC. All the samples indicated that they contain 2% by weight of safranal through the methodology used according to the ISO3632. The HPLC analysis was carried out in the same way as in Example 1 for the saffron extracts of the invention (Table 2).

TABLE 2

HPLC analysis according to the method described in Example 1 of different commercial samples (A-E) of saffron extracts certificated at 2% in safranal according to the ISO3632 Standard.

| Commercial Samples | HPLC Analysis | | |
|---|---|---|---|
| 2% safranal (ISO3632) | Safranal (%) | Crocins (%) | Σ* (%) |
| A | 0.007 | 0.619 | 0.626 |
| B | 0.006 | 0.384 | 0.390 |
| C | 0.000 | 1.929 | 1.929 |
| D | 0.007 | 2.450 | 2.457 |
| E | 0.006 | 0.443 | 0.450 |

*Sum of Safranal and Crocins analyzed by HPLC according to formula (1)

As can be observed in Table 2, all the samples are standardized to 2% safranal by dry weight according to the ISO3632, but the chromatographic analysis shows that the safranal content is considerably below this amount, even this active substance is completely absent in one of the analyzed extracts (Sample C). Moreover, the crocin concentration varies greatly, despite the fact that all the samples were standardized to 2% in safranal through the ISO3632 standard.

These data reveal the need to carry out further specific quantitative analyses such as the HPLC methodology described above to evaluate the active substances in saffron extracts.

Example 3—Clinical Trial

In another preferred modality, a parallel, placebo-controlled, double-blind clinical trial was conducted in healthy participants, with the aim of determining the effective dosage of the active substances present in the extract of the present invention, which have an effect on the prevention of mood disorders related to depression.

Methodology

The following example describes the composition of the tablets that the participants included in the clinical trial received. As may be seen in Table 3, the new saffron extract was transmitted in two dosages, one of 28 mg/day and another of 22 mg/day, divided into two daily administrations, which along with the placebo group, formed the three treatment groups to be studied.

TABLE 3

Composition of the saffron extract object of the present invention and of the placebo, present in the tablets used in the clinical trial.

| Formula offered in the clinical trial | Daily Dosage (in tablets) | | |
|---|---|---|---|
| | 2 × 14 mg | 2 × 11 mg | Placebo 2 × 0 mg |
| Extract of the invention | 14.0 | 11.0 | 0.0 |
| Excipients | | | |
| Red iron oxide | 0.0 | 0.0 | 0.1 |
| Microcrystalline cellulose | 187.0 | 190.0 | 176.9 |
| Calcium hydrogen phosphate | 144.0 | 144.0 | 144.0 |
| Carrot extract | 0.0 | 0.0 | 22.0 |
| Povidone | 5.0 | 5.0 | 5.0 |
| Croscarmellose sodium | 9.0 | 9.0 | 9.0 |
| Colloidal anhydrous silica | 3.0 | 3.0 | 4.0 |
| Magnesium stearate | 3.0 | 3.0 | 4.0 |
| Coating | | | |
| Hypromellose | 9.0 | 9.0 | 9.0 |
| Macrogol 8000 | 3.7 | 3.7 | 3.7 |
| Red iron oxide | 2.3 | 2.3 | 2.3 |
| Carnauba wax | q.s. | q.s. | q.s. | q.s.: quantum sufficit

In this study, the effectiveness of the saffron extract object of the present invention for improving general mood, reducing feelings of stress, anxiety, fatigue, and increasing vitality and sleep quality in healthy adults was studied.

In the clinical trial, 128 individuals (healthy men and women aged between 18 and 77, self-diagnosed, with subsequent confirmation by doctors, with low mood but not depression) took part in order to study the effect of the new saffron extract during one month of treatment. The participants were divided into three groups to which the saffron extract of the present invention was supplied in tablet form with a dosage of 28 mg/day, 22 mg/day, or a placebo treatment, respectively, as may be seen in Table 4. Each subject received precise instructions by the doctors to take two tablets per day for four weeks (one table with lunch and another with dinner).

TABLE 4

Demographic data on the participants at the beginning of the clinical trial.

| Demographic data | Treatment groups | | | |
|---|---|---|---|---|
| | Total (n = 121) | 28 mg/day (n = 41) | 22 mg/day (n = 42) | Placebo (n = 38) |
| Age | | | | |
| Mean (SD) | 39.1 (13.77) | 40.4 (12.71) | 36.7 (14.59) | 40.38 (13.97) |
| Range of variation | 18-77 | 21-68 | 18-77 | 23-68 |
| Sex (Number, %) | | | | |
| Women | 75 (62.0%) | 26 (63.4%) | 26 (61.9%) | 23 (60.5%) |
| Men | 46 (38.0%) | 15 (36.6%) | 16 (38.1%) | 15 (39.5%) |
| Status (Number, %) | | | | |
| Married | 74 (61.2%) | 25 (61.0%) | 27 (64.3%) | 22 (57.9%) |
| Single | 47 (38.8%) | 16 (39.0%) | 15 (35.7%) | 16 (42.1%) |
| Work (Number, %) | | | | |
| Employed/student | 103 (85.1%) | 34 (82.9%) | 37 (88.1%) | 32 (84.2%) |
| Unemployed/retired | 18 (14.9%) | 7 (17.1%) | 5 (11.9%) | 6 (15.8%) |
| Weight Mean kg (SD) | 76.34 (17.22) | 75.89 (16.48) | 77.54 (18.20) | 75.56 (17.39) |
| Body Mass Index Mean (SD) | 26.42 (6.33) | 26.74 (5.90) | 27.01 (7.91) | 25.38 (4.77) |
| Smoker (Number, %) | | | | |
| Yes | 17 (14.0%) | 8 (19.5%) | 6 (14.3%) | 3 (7.9%) |
| No | 104 (86.0%) | 33 (80.5%) | 36 (85.7%) | 35 (92.1%) |
| Alcohol (Number, %) | | | | |
| Less than 3 per week | 44 (36.4%) | 14 (36.1%) | 12 (28.6%) | 18 (47.4%) |
| More than 3 per week | 77 (63.6%) | 27 (65.9%) | 30 (71.4%) | 20 (52.6%) |
| Exercise per week | | | | |

TABLE 4-continued

Demographic data on the participants at the beginning of the clinical trial.

| | | Treatment groups | | |
|---|---|---|---|---|
| Demographic data | Total (n = 121) | 28 mg/day (n = 41) | 22 mg/day (n = 42) | Placebo (n = 38) |
| Yes (Number, %) | 85 (70.2%) | 29 (70.7%) | 27 (64.3%) | 29 (76.3%) |
| No (Number, %) | 36 (29.8%) | 12 (29.3%) | 15 (35.7%) | 9 (23.7%) |

No significant differences were seen between groups at the start of the treatment (p > 0.01, two-tailed)
SD: Standard deviation The study was revised and approved by the Queensland Clinical Research Ethics Committee and registered in the Australian New Zealand Clinical Trials Registry (approval number HREC2014002), protected by current legislation, in the National Health and Medical Research Council; Australia). The participants were evaluated by doctors following the inclusion and exclusion criteria approved by the Ethics Committee of the present clinical trial.

After a first interview with the doctor, people diagnosed with a mood disorder such as MDD (Major Depressive Disorder), bipolar disorder or any other type of disorder that may have given positive results for depression in the Beck Depression Inventory (Beck et al., 1988) were excluded. People suffering from insomnia or working night shifts and were unable to have a normal night's sleep, or suffering from severe premenstrual syndrome with mood changes and/or pain that may mask the results during the study period, as well as people suffering from any neurological disorders or taking nutritional diet supplements, including herbs, that may affect mood, such as St. John's wort, tryptophan, S-adenosyl methionine, 5-hydroxytryptophan, melatonin and γ-aminobutyric acid, were excluded. People that were taking a saffron supplement or could not exclude saffron or food containing saffron from their diet were also excluded. Furthermore, candidates that showed signs of any type of known hypersensitivity to medicaments or nutritional supplements, foods or if they were receiving heparin, warfarin, dalteparin, enoxaparin or other similar anticoagulant therapy, that had been diagnosed with hypertension or were being treated with antihypertensive drugs, with kidney or liver failure, or any other type of illness, alcohol problems or drug use were excluded. Individuals who were participating or had participated in another clinical trial in the last 30 days were also excluded.

After analyzing 137 potential participants under the exclusion criteria, 128 healthy adults between the ages of 18-77 were randomly assigned into three groups. Seven participants abandoned the study, the study reaching the end of the experimental stage with 121 active participants, 28 mg/day (n=41), 22 mg/day (n=42), and the placebo (n=38).

The effect of the saffron extract of the invention on mood was evaluated by using the following indicators, which are extensively described in medical literature and clinical psychology: POMS (Profile of Mood States), PANAS (The Positive and Negative Affect Schedule) and DASS (Depression Anxiety Stress States). Sleep was controlled by the PSQI index (Pittburgh Sleep Quality Index).

The POMS (Profile of Mood States. McNair et al., 1971) analysis, used in the clinical study to evaluate initial mood, consists of 65 items, with adjectives that describe an emotion (for example, sad, angry, happy), on a five-point scale for each one, where 0=not at all; 1=a little; 2=moderately; 3=quite a bit; and 4=extremely (except for relaxed and efficient items, which were recorded inversely). The participants were asked how they felt at that moment, and the answers were grouped into six subcategories; 5 negative (tension, depression, anger, fatigue and confusion) and 1 positive (vigor). For each participant, the "Total Mood Disturbance" (TMD, which includes Tension+Depression+Anger+Fatigue+Confusion−Vigor) was calculated, projecting a general vision of the mood of the individual. The score variation from the beginning (baseline) to week 4 of the study was calculated for each subscale, with the aim of reducing the variance within the groups (Davidson et al., 2002; Edwards and Haythornthwaite, 2004). The score variations during the treatment with respect to TMD ranged from −232 to 200 (a positive result indicated an increase in depression, while a negative value indicated a decrease in depression).

As a secondary method, PANAS (Watson and Clark, 1994) was used, which is an indicator consisting of 20 items; 10 positive words (for example, excited, proud, alert . . . ) and 10 negative words (for example, hostile, irritable, afraid, etc.), scored on a 5-point scale that is the same as POMS. Participants were asked how they felt compared to the previous week and the answers were grouped into two subscales (Positive Affect, PA, and Negative Affect, NA). The score variation range for PA and NA was from −40 to 40.

Another secondary analysis method used was that which corresponds to the Depression Anxiety Stress States or DASS-21 (Lovibond and Lovibond, 1995), which consists of 21 items divided into three subscales that correspond to depression, anxiety and stress (each one with 7 self-report items). Participants were asked how they felt during the previous week and each item was scored from 0 to 3, where 0=never; 1=sometimes; 2=often; and 3=almost always.

The PSQI or Pittsburgh Sleep Quality Index (Buysse et al., 1989) is designed to measure sleep quality through 19 self-classification questions and five questions proposed by people who have frequent and direct contact with the study participant, whenever it was possible.

The statistical analyses were carried out through the SPSS 23.0 program with a level of significance $\alpha<0.05$. The different score variations of each of the parameters studied, related to mood and sleep, were calculated for each of the participants included in the clinical trial (Davidson et al., 2002; Edwards and Haythornthwaite, 2004).

Results

POMS

Figure 2:
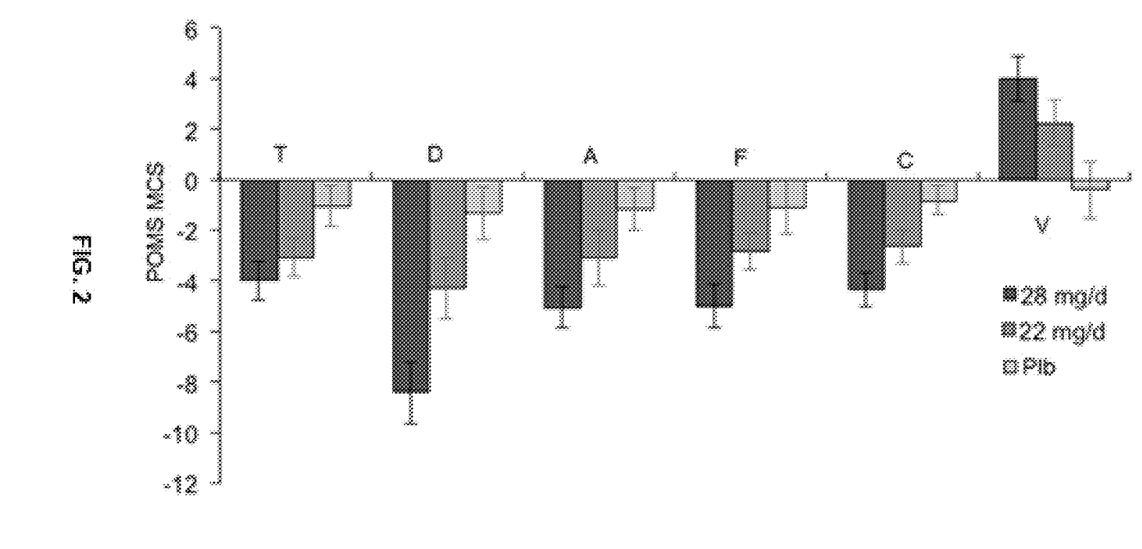
FIG. 2. Changes in the mean POMS values showing five negative subcategories (T: tension; D: depression; A: anger; F: fatigue; C: confusion) and one positive (V: vigour). POMS MCS: POMS Mean Change Score; Plb: Placebo.

FIG. 2 shows the results obtained for each of the emotions analyzed during the treatment period in the three study groups (treatment with saffron extract in dosages of 28 mg/day or 22 mg/day, and placebo). Gabriel's Post Hoc Test showed a significant improvement in all the POMS subscales of the treatment with saffron extract in the change scores for the group treated with 28 mg/day of the saffron extract of the present invention.

For the case of "Tension", a significant improvement was noted at the end of the treatment period, $F (2.113)=3.82$; $p=0.025$. Gabriel's Post Hoc Test revealed that the group taking 28 mg/day of the saffron extract was four-fold less tense than the placebo group (improvement of −1.06 to −4.00, FIG. 2). The same happened for the "Depression" subscale with $F (2.113)=9.46$, $p<0.001$, $\omega=0.36$ (large effect); the group treated with 28 mg/day of the saffron extract significantly improved, being sixfold less depressed at the end of the treatment compared to the placebo group as can be seen in FIG. 2 (improvement of −1.33 to −8.43).

The same trend was seen for the subscales "Anger", with values $F (2.112)=4.39$, $p=0,010$, $\omega=0.26$ (intermediate effect); "Fatigue", with $F (2.113)=4.92$, $p=0.009$, $\omega=0.25$ (intermediate effect) and "Confusion", with $F (2.113)=7.81$, $p=0.001$, $\omega=0.32$ (intermediate effect). The treatment with 28 mg/day of the saffron extract showed a significant five-fold reduction compared to the placebo group, anger (from −1.14 to −5.05), fatigue (from −1.11 to −5.00) and confusion (from −0.83 to −4.35; FIG. 2).

The POMS "vigor" subscale showed a significant improvement on an inverse scale, with a value of $F (2.112)=5.25$, $p=0.007$, $\omega=0.26$ (intermediate effect). The group treated with 28 mg/day of the saffron extract experienced a significant increase in "vigor" at the end of the treatment, improving by tenfold the vigor scale compared to the placebo group (from −0.39 to +4.00; FIG. 2).

Figure 3:
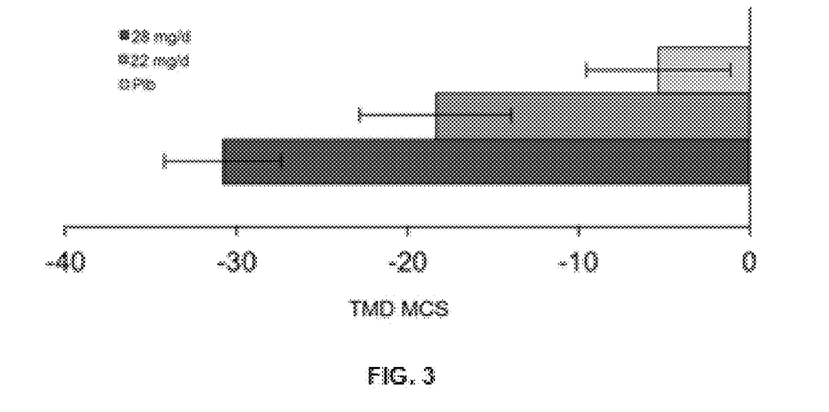
FIG. 3. Changes in the POMS values showing the values of the Total Mood Disturbance, TMD MCS analysis: Total Mood Disturbance Mean Change Score; Plb Placebo.

FIG. 3 represents the average variation corresponding to the Total Mood Disturbance (TMD) analysis for each of the study groups during the month of treatment with the saffron extract of the present invention $F (2.111)=9.94$, $p<0.001$, $\omega=0.37$ (large effect). Specifically, the group treated with 28 mg/day of the saffron extract significantly reduced its TMD level, approximately sixfold compared to the placebo group (from −5.37 to −30.83; FIG. 3).

PANAS

Figure 4:
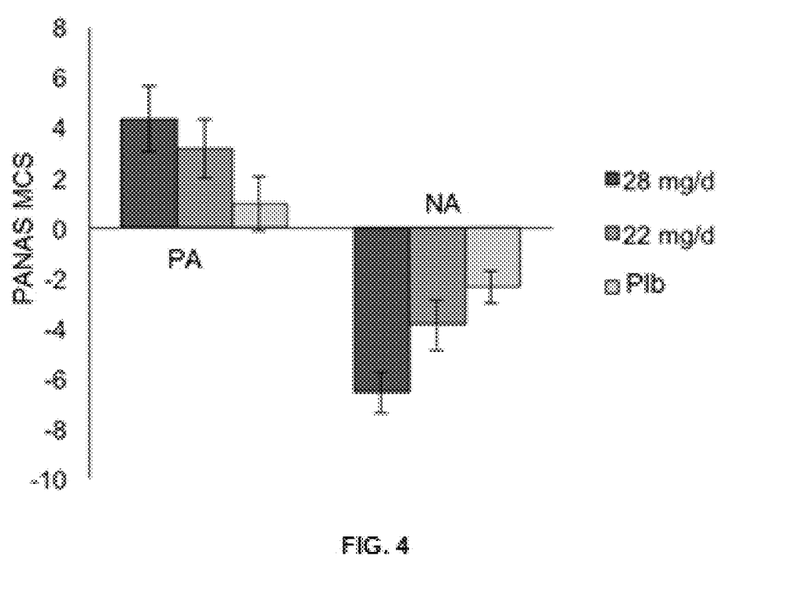
FIG. 4. Changes in the mean PANAS values for evaluating Positive Affect and Negative Affect. PANAS MCS: PANAS Mean Change Score; Plb Placebo; PA: Positive Affect; NA: Negative Affect.

FIG. 4 shows the average change values for the PANAS analysis, which although they are not significant, show a clear trend for the "Positive Affect" (or Positive Mood) and "Negative Affect" (or Negative Mood), indicating an improvement in mood in the groups treated with both the 22 mg/day and 28 mg/day dosages with the saffron extract of the present invention, with respect to the placebo group, after one month of treatment.

The variance analysis (ANOVA) showed a significant difference in the treatment, between the study groups in the scores related to Negative Affect, $F (2.111)=6.97$, $p=0.001$, $\omega=0.31$ (intermediate effect). The variation of the "Negative Affect" value in the group treated with 28 mg/day of the saffron extract, significantly improved by threefold compared to the placebo group (from −2.40 to −6.63), $p=0.001$, $d=-0.42$ (intermediate effect, according to Cohen's conventions).

DASS

The ANOVA treatment was also carried out with the DASS test in order to analyze the variations observed in the subscales: depression, anxiety and stress among the different treatment groups.

Figure 5:
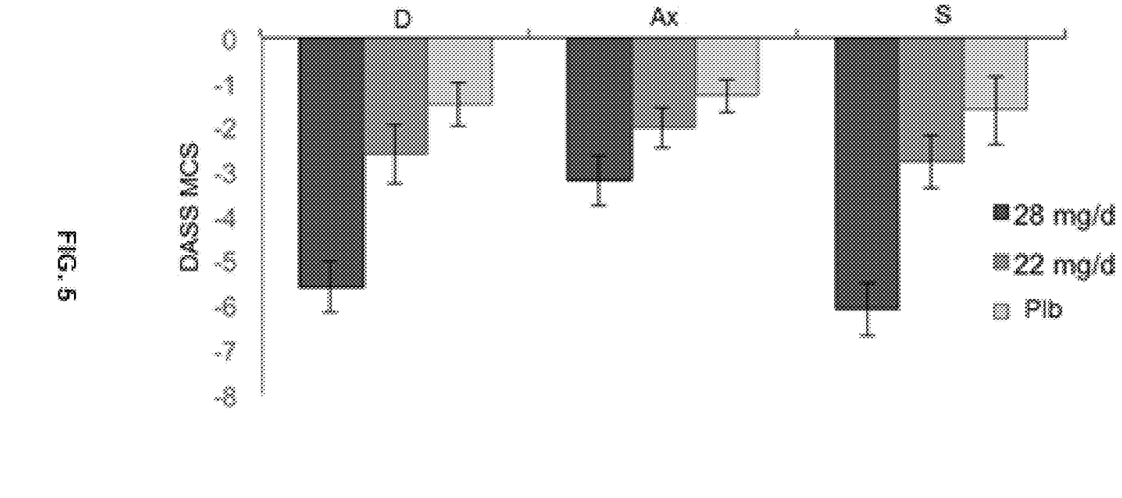
FIG. 5. Changes in the mean DASS values for evaluating depression (D), anxiety (Ax) and stress (S). DASS MCS: DASS Mean Change Score; Plb: placebo.

For the change scores in the specific case of the DASS depression subscale, a significant effect was noted with $F (2.118)=12.96$, $p<0.001$, $\omega=0.41$ (large effect). As can be seen in FIG. 5, the group treated with 28 mg/day of the saffron extract of the present invention improved significantly with respect to the placebo group, reducing fourfold the symptoms related to a depressive condition (values from −1.42 to −5.61). A dosage dependent effect was also observed, obtaining a significant improvement in participants treated with 28 mg/day compared to those treated with 22 mg/day of the saffron extract, which halved the symptoms related to depression (values from −2.87 to −5.61).

For the anxiety subscale, the treatment also showed a significant improvement, $F (2.118)=4.33$, $p=0.01$, $\omega=0.23$ (intermediate effect). According to Gabriel's Post Hoc Test, there was a significant reduction in anxiety of almost threefold in the group treated with 28 mg/day of the saffron extract compared to the placebo group, after one month of treatment (improvement of −1.23 to −3.22; FIG. 5).

In the case of the DASS stress subscale, a significant change was also observed after treatment with the saffron extract, $F (2.118)=14.29$, $p<0.001$, $\omega=0.42$ (large effect). The group treated with 28 mg/day of the present extract significantly improved the stress condition with respect to the rest of the groups studied. Specifically, the signs of stress at the end of the treatment were reduced by twofold and fourfold, compared to the group treated with 22 mg/day (reduction from −3.11 to −6.12) and to the placebo group (reduction from −1.49 to −6.12), respectively.

Similarly to the effect of the treatment on the "Mood" component, the effect of the saffron extract of the present invention was also noteworthy in the component corresponding to "Sleep" quality, which was evaluated through the Pittsburgh index (PSQI). After carrying out the ANOVA statistical analysis on score variations in the overall PSQI, a significant improvement was observed in the sleep of the group treated with 28 mg/day in the overall PSQI change score, $F (2.106)=4.27$, $p=0.016$, compared to the placebo group.

CONCLUSION

The results obtained in the clinical trial expand the scientific literature since it is the first such trial that has been carried out with healthy people. Furthermore, it shows that the saffron extract of the invention obtained at industrial scale, analyzed through HPLC, does not have any secondary or undesirable effect on the organism, but does show significant positive effects in all the psychological studies carried out to analyze mood at the end of the treatment (POMS-TMD, PANAS, DASS and PSQI).

With regards to the dosage, it was possible to observe a clear dosage-dependent relationship between the two concentrations that were studied, which means that this study is one of the first to identify a clinically appropriate and empirically justified dosage schedule. The effects of the saffron extract, object of the present patent specification, on mood were consistent in both sexes, and they have been achieved without adverse effects on the performance or safety parameters.

REFERENCES

Alonso, G L., Salinas, M R., Garuo, J., Sanchez-Fernandez, M A. (2001). Composition of crocins and picrocrocin from Spanish Saffron (*Crocus sativus* L.). Journal of Food Quality, 24, 219-233.

Akhondzadeh, S., Fallah-Pour, H., Afkham, K., Jamshidi, A H., Khalighi-Cigaroudi, F. (2004). Comparison of *Crocus sativus* L, and imipramine in the treatment of mild to moderate depression: A pilot double-blind randomized trial. BMC Complementary and Alternative Medicine 4, 12.

Akhondzadeh, S., Tahmacebi-Pour, N., Noorbala, A A., Amini, H., Fallah-Pour, H., Jamshidi, A H., Khani, M. (2005). *Crocus sativus* L, in the Treatment of Mild to Moderate Depression: A Double-blind, Randomized and Placebo-controlled Trial. Phytotherapy Research, 19, 148-151.

Akhondzadeh B A., Ghoreishi S A., Noorbala A A., Akhondzadeh, S H., Rezazadeh S H. (2008). Petal and Stigma of Crocus sativus L, in the Treatment of Depression: A Pilot Double-blind Randomized Trial. Journal of Medicinal Plants, 7, 29-36.

Basti, A A., Moshiri, E., Noorbala, A A., Jamshidi, A H., Abbasi, S H., Akhondzadeh, S. (2007), Comparison of petal of Crocus sativus L, and fluoxetine in the treatment of depressed outpatients: A pilot double-blind randomized trial. Progress in Neuro-Psychopharmacology & Biological Psychiatry, 31, 439-442.

Beck, A T., Steer, R A., Garbin, M G. (1988). Psychometric properties of the Beck Depression Inventory: Twenty-five years of evaluation. Clinical Psychology Review, 8, 77-100.

Bisschop, M I., Kriegsmana, D M W., Beekman, A T F., Deeg, D J H. (2004). Chronic diseases and depression: the modifying role of psychosocial resources. Social Science & Medicine, 59, 721-733.

Buysse, D J., Reynolds, C F., Monk, T H., Berman, S R., Kupfer, D J. (1989). The Pittsburgh Sleep Quality Index: A new instrument for psychiatric practice and research. Psychiatry Research 28, 193-213.

Caballero-Ortega, H., Pereda-Miranda, R., Abdullaev, F I. (2007). HPLC quantification of major active components from 11 different saffron (Crocus sativus L,) sources. Food Chemistry 100, 1126-1131.

Carr, G V., Schechter, L E., Lucki, I. (2011). Antidepressant and anxiolytic effects of selective 5-HT6 receptor agonists in rats. Psychopharmacology, 213, 499-507.

Davidson, R J., Sherer, K R. and Goldsmith, H H. (2002). Handbook of Affective Sciences (1st ed,), USA: Oxford University Press.

Edwards, R R., Haythornthwaite, J. (2004). Mood swings: Variability in the use of the Profile of Mood States, J Pain Symptom Manage 28, 534.

Ettehadi, H., Mojabi, S N., Ranjbaran, M., Shams, J., Sahraei, H., Hedayati, M., Asefi, F. (2013). Aqueous Extract of Saffron (Crocus sativus) Increases Brain Dopamine and Glutamate Concentrations in Rats. Journal of Behavioral and Brain Science, 3, 315-319.

Fava, M., Katharine, M D., Davidson, G. (1996). Definition and epidemiology of treatment-resistant depression, Psychiatric Clinics of North America, 19, 179-200.

Fava, M. (2003). Diagnosis and definition of treatment-resistant depression. Biological Psychiatry, 53, 649-659.

Ferguson, J M. (2001). SSRI Antidepressant Medications: Adverse Effects and Tolerability. Primary Care Companion—Journal of Clinical Psychiatry, 3, 22-27.

Haddad, P M. (2005). Do antidepressants cause dependence? Epidemiologia e Psichiatria Sociale, 14, 2.

Hamilton, M. (1960). A rating scale for depression. Journal of Neurology, Neurosurgery and Psychiatry, 23, 56-62.

Hosseinzadeh, H., Karimi, G., Niapoor, M. (2004). Antidepressant effect of Crocus sativus I, stigma extracts and their constituents, crocin and Safranal, in mice, Acta Horticulturae, 650, 435-45.

International Standard, Saffron specification, ISO-3632-1980(E). International Organization for Standardization, Geneva. International Standard, Saffron specification, ISO 3632-1 and ISO 3632-2: 1993(E). International Organization for Standardization, Geneva, 1993.

Karimi, G H R., Hosseinzadeh, H., Khalegh Panah, P. (2001). Study of antidepressant effect of aqueous and ethanolic extract of Crocus sativus in mice. Iranian journal of basic medical sciences, 4, 11-15.

Kashani, L., Raisi, F., Saroukhani, S., Sohrabi, H., Modabbernia, A., Nasehi, A A., Jamshidi, A., Ashrafi, M., Mansouri, P., Ghaeli, P., Akhondzadeh, S. (2013). Saffron for treatment of fluoxetine-induced sexual dysfunction in women: randomized double-blind placebo-controlled study. Human Psychopharmacology Clinical and Experimental Journal, 28, 54-60.

Lech, K., Witowska-Jarosz, J., Jarosz, M. (2009). Saffron yellow: characterization of carotenoids by high performance liquid chromatography with electrospray mass spectrometric detection. Journal of Mass Spectrometry, 44, 1661-1667.

Leonard, B. and Maes, M. (2012). Mechanistic explanations how cell-mediated immune activation, inflammation and oxidative and nitrosative stress pathways and their sequels and concomitants play a role in the pathophysiology of unipolar depression. Neuroscience & Biobehavioral Reviews, 36, 764-785.

Lopresti, A L. and Drummond, P D. (2014). Saffron (Crocus sativus) for depression: a systematic review of clinical studies and examination of underlying antidepressant mechanisms of action. Human Psychopharmacology: Clinical and Experimental, 29, 517-527.

Lovibond, S, H., and Lovibond, P F. (1995). The structure of negative emotional states: comparison of the depression anxiety stress scales (DASS) with the beck depression and anxiety inventories. Behaviour research and therapy, 33, 335-343.

Maes, M., Galecki, P., Chang, Y S., Berk, M. (2011). A review on the oxidative and nitrosative stress (O&NS) pathways in major depression and their possible contribution to the (neuro) degenerative processes in that illness. Progress in Neuro-Psychopharmacology & Biological Psychiatry 35, 676-692.

Maes, M., Fišar, Z., Medina, M., Scapagnini, G., Nowak, M., Berk, M. (2012). New drug targets in depression: inflammatory, cell-mediated immune, oxidative and nitrosative stress, mitochondrial, antioxidant, and neuroprogressive pathways, and new drug candidates—Nrf2 activators and GSK-3 inhibitors, Inflammation In Acute And Chronic Neurological And Psychiatric Diseases. Inflammopharmacology, 20, 127-150.

McNair, D M., Lorr, M. and Droppleman, L F. (1971). Manual: Profile of Mood States, San Diego, Calif.: Educational and Industrial Testing Service.

Moshiri, E., Basti, A A., Noorbala, A A., Jamshidi, A H., Abbasi, S H., Akhondzadeh, S. (2006). Crocus sativus L, (petal) in the treatment of mild-to-moderate depression: A double-blind, randomized and placebo-controlled trial. Phytomedicine, 13, 607-611.

Moussavi, S., Chatterji, S., Verdes, E., Tandon, A., Patel, V., Ustun, B. (2007). Depression, chronic diseases, and decrements in health: results from the World Health Surveys, Lancet, 370, 851-858.

Noorbala, A A., Akhondzadeha, S., Tahmacebi-Pour, N., Jamshidi, A H. (2005). Hydro-alcoholic extract of Crocus sativus L, versus fluoxetine in the treatment of mild to moderate depression: a double-blind, randomized pilot trial. Journal of Ethnopharmacology 97, 281-284.

Ordundi, S A. and Tsimidou, M Z. (2004), Saffron quality: effect of agricultural practices, processing and storage, Production Practices and Quality Assessment of Food Crops, 1, 209-260.

Orfanou, O. and Tsimidou, M Z. (1996). Evaluation of the colouring strength of saffron spice by UV-Vis spectrometry. Food Chemistry, 57, 463-469.

Palta, P., Samuel, L J., Miller, E R., Szanton, S L. (2014). Depression and Oxidative Stress: Results from a meta-analysis of observational studies. Psychosomatic Medicine, 76, 12-19.

Shahmansouri, N., Farokhnia, M., Abbasi, S H., Kassaian, S E., Noorbala, S A., Gougol, A., Yekehtaz, H., Forghani, S., Mahmoodian, M., Saroukhani, S., Arjmandi-Beglar, A., Akhondzadeh, S. (2014). A randomized, double-blind, clinical trial comparing the efficacy and safety of *Crocus sativus* L, with fluoxetine for improving mild to moderate depression in post percutaneous coronary intervention patients. Journal of Affective Disorders, 155, 216-222.

Serretti, A., Kato, M., Ronchi, D., Kinoshita, T. (2007). Meta-analysis of serotonin transporter gene promoter polymorphism (5-HTTLPR) association with selective serotonin reuptake inhibitor efficacy in depressed patients. Molecular Psychiatry, 12, 247-257.

Singleton, V L. and Rossi, J A. (1965), Colorimetry of total phenolics with phosphomolybdic-phosphotungstic acid reagents. American Journal of Enology and Viticulture, 16, 144-158.

Tarantilis, P A., Tsoupras, G., Polisiou, M. (1995). Determination of saffron (*Crocus sativus* L.) components in crude plant extract using high-performance liquid chromatography-UV-visible photodiode-array detection-mass spectrometry. Journal of Chromatography A, 699, 107-118.

Ulbricht, C., Conquer, J., Costa, D., Hollands, W., Iannuzzi, C., Isaac, R., Jordan, J K., Ledesma, N., Ostroff, C., Serrano, J M G., Shafferh, M D., Varghese, M. (2011). An Evidence-Based Systematic Review of Saffron (*Crocus sativus*) by the Natural Standard Research Collaboration. Journal of Dietary Supplements, 8, 58-114.

Vanderkooy, J D., Kennedy, S H., Bagby, R M. (2002). Antidepressant side effects in depression patients treated in a naturalistic setting: a study of bupropion, moclobemide, paroxetine, sertraline, and venlafaxine. Canadian Journal of Psychiatry, Revue Canadienne de Psychiatrie, 47, 174-180.

Watson, D. and Clark, L A. (1994). The PANAS-X Manual for the Positive and Negative Affect Schedule—Expanded Form, Unsure, 277, 1-27.

The invention claimed is:

1. A method for treatment of low mood, comprising administering to a subject in need thereof a therapeutically effective amount of a composition comprising an extract of saffron stigmas analyzed by HPLC, the composition comprising:
   a) between 0.03% and 1% dry weight of safranal, and
   b) at least 3.48% dry weight of crocins, wherein said crocins comprise trans-crocin-4, trans-crocin-3, trans-crocin-2', cis-crocin-4, trans-crocin-2, and/or trans-crocin-1.

2. The method according to claim 1, wherein the composition is administered orally.

3. The method according to claim 1, wherein the composition is administered in a dosage greater than 15 mg/day.

4. The method according to claim 1, wherein the composition is administered in a daily dosage of 28 mg/day.

* * * * *

(12) EX PARTE REEXAMINATION CERTIFICATE (11906th)
United States Patent
Inarejos Garcéa et al.

(10) Number: US 10,933,110 C1
(45) Certificate Issued: Aug. 30, 2021

(54) SAFFRON EXTRACT AND ITS USE FOR THE PREVENTION OF MOOD DISORDERS RELATED TO DEPRESSION

(71) Applicant: PHARMACTIVE BIOTECH PRODUCTS, S.L., Madrid (ES)

(72) Inventors: Antonio Manuel Inarejos Garcéa, Madrid (ES); Marin Prodanov Prodanov, Madrid (ES); Amanda Rao, Madrid (ES); Jean-Marie Raymond, Madrid (ES)

(73) Assignee: PHARMACTIVE BIOTECH PRODUCTS, S.L., Madrid (ES)

Reexamination Request:
No. 90/014,738, Apr. 26, 2021

Reexamination Certificate for:
Patent No.: 10,933,110
Issued: Mar. 2, 2021
Appl. No.: 16/087,585
PCT Filed: Apr. 17, 2017
PCT No.: PCT/ES2017/070237
§ 371 (c)(1),
(2) Date: Sep. 21, 2018
PCT Pub. No.: WO2017/182688
PCT Pub. Date: Oct. 26, 2017

(30) Foreign Application Priority Data

Apr. 18, 2016 (ES) ............... ES201630491

(51) Int. Cl.
*A61K 36/88* (2006.01)
*A23L 29/206* (2016.01)
*A23L 33/105* (2016.01)
*A61K 31/7034* (2006.01)
*A61K 31/7024* (2006.01)
*A61K 31/05* (2006.01)
*A61K 9/20* (2006.01)
*A61P 25/24* (2006.01)
*A61K 9/00* (2006.01)
*A61K 31/11* (2006.01)

(52) U.S. Cl.
CPC ............ *A61K 36/88* (2013.01); *A23L 29/206* (2016.08); *A23L 33/105* (2016.08); *A61K 9/0053* (2013.01); *A61K 9/2054* (2013.01); *A61K 31/05* (2013.01); *A61K 31/11* (2013.01); *A61K 31/7024* (2013.01); *A61P 25/24* (2018.01); *A23V 2002/00* (2013.01); *A23V 2200/322* (2013.01); *A23V 2250/211* (2013.01); *A23V 2250/2132* (2013.01)

(58) Field of Classification Search
None
See application file for complete search history.

(56) References Cited

To view the complete listing of prior art documents cited during the proceeding for Reexamination Control Number 90/014,738, please refer to the USPTO's public Patent Application Information Retrieval (PAIR) system under the Display References tab.

*Primary Examiner* — Bruce R Campell

(57) ABSTRACT

The present invention relates to a powdered composition obtained from saffron stigmas characterized in that it comprises from 0.03% to 1% dry weight of safranal; and at least 3.48% dry weight of crocins that encompasses the various trans-crocin-4 (major isomer), trans-crocin-3, trans-crocin-2', cis-crocin-4, trans-crocin-2, trans-crocin-1 isomers and any of their mixtures.

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1-4 is confirmed.

\* \* \* \* \*